(12) United States Patent
Wu

(10) Patent No.: US 8,752,268 B2
(45) Date of Patent: Jun. 17, 2014

(54) METHOD OF MAKING STENTS WITH RADIOPAQUE MARKERS

(71) Applicant: Abbott Cardiovascular Systems Inc., Santa Clara, CA (US)

(72) Inventor: Patrick P. Wu, San Carlos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/964,008

(22) Filed: Aug. 9, 2013

(65) Prior Publication Data

US 2013/0325106 A1  Dec. 5, 2013

Related U.S. Application Data

(63) Continuation of application No. 11/796,226, filed on Apr. 26, 2007.

(60) Provisional application No. 60/809,088, filed on May 26, 2006.

(51) Int. Cl.
*B23P 11/00* (2006.01)
*A61F 2/06* (2013.01)

(52) U.S. Cl.
USPC .................. 29/458; 29/508; 29/516; 29/517; 623/1.34

(58) Field of Classification Search
USPC .................. 623/1.34; 29/458, 508, 516, 517
See application file for complete search history.

(56) References Cited

U.S. PATENT DOCUMENTS

| 2,697,863 | A | 12/1954 | Moser |
| 3,476,463 | A | 11/1969 | Kreuzer |
| 3,687,135 | A | 8/1972 | Stroganov et al. |
| 3,839,743 | A | 10/1974 | Schwarcz |
| 3,900,632 | A | 8/1975 | Robinson |
| 4,104,410 | A | 8/1978 | Malecki |
| 4,110,497 | A | 8/1978 | Hoel |
| 4,321,711 | A | 3/1982 | Mano |
| 4,346,028 | A | 8/1982 | Griffith |
| 4,596,574 | A | 6/1986 | Urist |
| 4,599,085 | A | 7/1986 | Riess et al. |
| 4,612,009 | A | 9/1986 | Drobnik et al. |
| 4,633,873 | A | 1/1987 | Dumican et al. |
| 4,656,083 | A | 4/1987 | Hoffman et al. |
| 4,718,907 | A | 1/1988 | Karwoski et al. |
| 4,722,335 | A | 2/1988 | Vilasi |

(Continued)

FOREIGN PATENT DOCUMENTS

| CN | 1241442 | 1/2000 |
| DE | 29724852 | 2/2005 |

(Continued)

OTHER PUBLICATIONS

Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).

(Continued)

*Primary Examiner* — Jermie Cozart
(74) *Attorney, Agent, or Firm* — Squire Sanders (US) LLP

(57) ABSTRACT

Various embodiments of stents with radiopaque markers arranged in patterns are described herein.

3 Claims, 8 Drawing Sheets

(56) References Cited

U.S. PATENT DOCUMENTS

| | | |
|---|---|---|
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,886,870 A | 12/1989 | D'Amore et al. |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,061,281 A | 10/1991 | Mares et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,976 A | 1/1995 | Couch |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,486,546 A | 1/1996 | Mathiesen et al. |
| 5,500,013 A | 3/1996 | Buscemi et al. |
| 5,502,158 A | 3/1996 | Sinclair et al. |
| 5,507,799 A | 4/1996 | Sumiya |
| 5,514,379 A | 5/1996 | Weissleder et al. |
| 5,525,646 A | 6/1996 | Lundgren et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,565,215 A | 10/1996 | Gref et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,603,722 A | 2/1997 | Phan et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,656,186 A | 8/1997 | Mourou et al. |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,686,540 A | 11/1997 | Kakizawa |
| 5,693,085 A | 12/1997 | Buirge et al. |
| 5,700,286 A | 12/1997 | Tartaglia et al. |
| 5,700,901 A | 12/1997 | Hurst et al. |
| 5,704,082 A | 1/1998 | Smith |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,725,572 A | 3/1998 | Lam et al. |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,327 A | 4/1998 | Frantzen |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,770,609 A | 6/1998 | Grainger et al. |
| 5,780,807 A | 7/1998 | Saunders |
| 5,800,516 A | 9/1998 | Fine et al. |
| 5,811,447 A | 9/1998 | Kunz et al. |
| 5,824,042 A | 10/1998 | Lombardi et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohtuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |

(56) References Cited

U.S. PATENT DOCUMENTS

| | | | |
|---|---|---|---|
| 5,877,263 A | 3/1999 | Patnaik et al. | |
| 5,879,713 A | 3/1999 | Roth et al. | |
| 5,888,533 A | 3/1999 | Dunn | |
| 5,891,192 A | 4/1999 | Murayama et al. | |
| 5,897,955 A | 4/1999 | Drumheller | |
| 5,906,759 A | 5/1999 | Richter | |
| 5,914,182 A | 6/1999 | Drumheller | |
| 5,916,870 A | 6/1999 | Lee et al. | |
| 5,922,005 A | 7/1999 | Richter et al. | |
| 5,942,209 A | 8/1999 | Leavitt et al. | |
| 5,948,428 A | 9/1999 | Lee et al. | |
| 5,954,744 A | 9/1999 | Phan et al. | |
| 5,957,975 A | 9/1999 | Lafont et al. | |
| 5,965,720 A | 10/1999 | Gryaznov et al. | |
| 5,971,954 A | 10/1999 | Conway et al. | |
| 5,976,182 A | 11/1999 | Cox | |
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,986,169 A | 11/1999 | Gjunter | |
| 5,997,468 A | 12/1999 | Wolff et al. | |
| 6,007,845 A | 12/1999 | Domb et al. | |
| 6,010,445 A | 1/2000 | Armini et al. | |
| 6,015,541 A | 1/2000 | Greff et al. | |
| 6,022,374 A | 2/2000 | Imran | |
| 6,042,606 A | 3/2000 | Frantzen | |
| 6,042,875 A | 3/2000 | Ding et al. | |
| 6,048,964 A | 4/2000 | Lee et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,066,156 A | 5/2000 | Yan | |
| 6,071,266 A | 6/2000 | Kelley | |
| 6,074,659 A | 6/2000 | Kunz et al. | |
| 6,080,177 A | 6/2000 | Igaki et al. | |
| 6,080,488 A | 6/2000 | Hostettler et al. | |
| 6,083,258 A | 7/2000 | Yadav | |
| 6,093,463 A | 7/2000 | Thakrar | |
| 6,096,070 A | 8/2000 | Ragheb et al. | |
| 6,096,525 A | 8/2000 | Patnaik | |
| 6,099,562 A | 8/2000 | Ding et al. | |
| 6,103,230 A | 8/2000 | Billiar et al. | |
| 6,107,416 A | 8/2000 | Patnaik et al. | |
| 6,110,188 A | 8/2000 | Narciso, Jr. | |
| 6,110,483 A | 8/2000 | Whitbourne | |
| 6,113,629 A | 9/2000 | Ken | |
| 6,117,979 A | 9/2000 | Hendriks et al. | |
| 6,120,536 A | 9/2000 | Ding et al. | |
| 6,120,904 A | 9/2000 | Hostettler et al. | |
| 6,121,027 A | 9/2000 | Clapper et al. | |
| 6,125,523 A | 10/2000 | Brown et al. | |
| 6,127,173 A | 10/2000 | Eckstein et al. | |
| 6,129,761 A | 10/2000 | Hubbell | |
| 6,129,928 A | 10/2000 | Sarangapani et al. | |
| 6,131,266 A | 10/2000 | Saunders | |
| 6,150,630 A | 11/2000 | Perry et al. | |
| 6,153,252 A | 11/2000 | Hossainy et al. | |
| 4,776,337 B1 | 12/2000 | Palmaz | |
| 6,156,062 A | 12/2000 | McGuinness | |
| 6,159,951 A | 12/2000 | Karpeisky et al. | |
| 6,160,084 A | 12/2000 | Langer et al. | |
| 6,160,240 A | 12/2000 | Momma et al. | |
| 6,165,212 A | 12/2000 | Dereume et al. | |
| 6,166,130 A | 12/2000 | Rhee et al. | |
| 6,169,170 B1 | 1/2001 | Gryaznov et al. | |
| 6,171,609 B1 | 1/2001 | Kunz | |
| 6,174,329 B1 * | 1/2001 | Callol et al. | 623/1.34 |
| 6,174,330 B1 | 1/2001 | Stinson | |
| 6,177,523 B1 | 1/2001 | Reich et al. | |
| 6,183,505 B1 | 2/2001 | Mohn, Jr. et al. | |
| 6,187,045 B1 | 2/2001 | Fehring et al. | |
| 6,210,715 B1 | 4/2001 | Starling et al. | |
| 6,224,626 B1 | 5/2001 | Steinke | |
| 6,228,845 B1 | 5/2001 | Donovan et al. | |
| 6,240,616 B1 | 6/2001 | Yan | |
| 6,245,076 B1 | 6/2001 | Yan | |
| 6,245,103 B1 | 6/2001 | Stinson | |
| 6,248,344 B1 | 6/2001 | Ylanen et al. | |
| 6,251,135 B1 | 6/2001 | Stinson et al. | |
| 6,251,142 B1 | 6/2001 | Bernacca et al. | |
| 6,254,632 B1 * | 7/2001 | Wu et al. | 623/1.15 |
| 6,260,976 B1 | 7/2001 | Endou et al. | |
| 6,273,913 B1 | 8/2001 | Wright et al. | |
| 6,281,262 B1 | 8/2001 | Shikinami | |
| 6,283,234 B1 | 9/2001 | Torbet | |
| 6,284,333 B1 | 9/2001 | Wang et al. | |
| 6,287,332 B1 | 9/2001 | Bolz et al. | |
| 6,290,721 B1 | 9/2001 | Heath | |
| 6,293,966 B1 | 9/2001 | Frantzen | |
| 6,295,168 B1 | 9/2001 | Hofnagle et al. | |
| 6,303,901 B1 | 10/2001 | Perry et al. | |
| 6,312,459 B1 | 11/2001 | Huang et al. | |
| 6,327,772 B1 | 12/2001 | Zadno-Azizi et al. | |
| 4,733,665 C2 | 1/2002 | Palmaz | |
| 6,334,871 B1 * | 1/2002 | Dor et al. | 623/1.34 |
| 6,355,058 B1 | 3/2002 | Pacetti et al. | |
| 6,361,557 B1 | 3/2002 | Gittings et al. | |
| 6,375,826 B1 | 4/2002 | Wang et al. | |
| 6,379,381 B1 | 4/2002 | Hossainy et al. | |
| 6,387,121 B1 | 5/2002 | Alt | |
| 6,388,043 B1 | 5/2002 | Langer et al. | |
| 6,395,326 B1 | 5/2002 | Castro et al. | |
| 6,409,752 B1 | 6/2002 | Boatman et al. | |
| 6,409,761 B1 | 6/2002 | Jang | |
| 6,423,092 B2 | 7/2002 | Datta et al. | |
| 6,461,632 B1 | 10/2002 | Gogolewski | |
| 6,464,720 B2 * | 10/2002 | Boatman et al. | 623/1.15 |
| 6,471,721 B1 | 10/2002 | Dang | |
| 6,475,779 B2 | 11/2002 | Mathiowitz et al. | |
| 6,479,565 B1 | 11/2002 | Stanley | |
| 6,485,512 B1 | 11/2002 | Cheng | |
| 6,492,615 B1 | 12/2002 | Flanagan | |
| 6,494,908 B1 | 12/2002 | Huxel et al. | |
| 6,495,156 B2 | 12/2002 | Wenz et al. | |
| 6,506,437 B1 | 1/2003 | Harish et al. | |
| 6,511,748 B1 | 1/2003 | Barrows | |
| 6,517,888 B1 | 2/2003 | Weber | |
| 6,521,865 B1 | 2/2003 | Jones et al. | |
| 6,527,801 B1 | 3/2003 | Dutta | |
| 6,537,589 B1 | 3/2003 | Chae et al. | |
| 6,539,607 B1 | 4/2003 | Fehring et al. | |
| 6,540,777 B2 | 4/2003 | Stenzel | |
| 6,554,854 B1 | 4/2003 | Flanagan | |
| 6,563,080 B2 | 5/2003 | Shapovalov et al. | |
| 6,563,998 B1 | 5/2003 | Farah | |
| 6,565,599 B1 | 5/2003 | Hong et al. | |
| 6,569,191 B1 | 5/2003 | Hogan | |
| 6,569,193 B1 | 5/2003 | Cox et al. | |
| 6,572,672 B2 | 6/2003 | Yadav et al. | |
| 6,574,851 B1 | 6/2003 | Mirizzi | |
| 6,582,472 B2 | 6/2003 | Hart | |
| 6,585,755 B2 | 7/2003 | Jackson et al. | |
| 6,589,227 B2 | 7/2003 | Sønderskov Klint | |
| 6,592,614 B2 | 7/2003 | Lenker et al. | |
| 6,592,617 B2 | 7/2003 | Thompson | |
| 6,613,072 B2 | 9/2003 | Lau et al. | |
| 6,620,194 B2 | 9/2003 | Ding et al. | |
| 6,626,936 B2 * | 9/2003 | Stinson | 623/1.15 |
| 6,626,939 B1 | 9/2003 | Burnside et al. | |
| 6,635,269 B1 | 10/2003 | Jennissen | |
| 6,645,243 B2 | 11/2003 | Vallana et al. | |
| 6,652,579 B1 * | 11/2003 | Cox et al. | 623/1.34 |
| 6,656,162 B2 | 12/2003 | Santini, Jr. et al. | |
| 6,664,335 B2 | 12/2003 | Krishnan | |
| 6,666,214 B2 | 12/2003 | Canham | |
| 6,667,049 B2 | 12/2003 | Janas et al. | |
| 6,669,722 B2 * | 12/2003 | Chen et al. | 623/1.15 |
| 6,669,723 B2 | 12/2003 | Killion et al. | |
| 6,676,697 B1 | 1/2004 | Richter | |
| 6,679,980 B1 | 1/2004 | Andreacchi | |
| 6,689,375 B1 | 2/2004 | Wahlig et al. | |
| 6,695,920 B1 | 2/2004 | Pacetti et al. | |
| 6,696,667 B1 | 2/2004 | Flanagan | |

(56) References Cited

U.S. PATENT DOCUMENTS

| | | | |
|---|---|---|---|
| 6,699,278 B2 * | 3/2004 | Fischell et al. | 623/1.15 |
| 6,706,273 B1 | 3/2004 | Roessler | |
| 6,709,379 B1 | 3/2004 | Brandau et al. | |
| 6,719,934 B2 | 4/2004 | Stinson | |
| 6,719,989 B1 | 4/2004 | Matsushima et al. | |
| 6,720,402 B2 | 4/2004 | Langer et al. | |
| 6,746,773 B2 | 6/2004 | Llanos et al. | |
| 6,752,826 B2 | 6/2004 | Holloway et al. | |
| 6,753,007 B2 | 6/2004 | Haggard et al. | |
| 6,764,505 B1 | 7/2004 | Hossainy et al. | |
| 6,780,261 B2 | 8/2004 | Trozera | |
| 6,801,368 B2 | 10/2004 | Coufal et al. | |
| 6,805,898 B1 | 10/2004 | Wu et al. | |
| 6,818,063 B1 | 11/2004 | Kerrigan | |
| 6,822,186 B2 | 11/2004 | Strassl et al. | |
| 6,846,323 B2 | 1/2005 | Yip et al. | |
| 6,852,946 B2 | 2/2005 | Groen et al. | |
| 6,858,680 B2 | 2/2005 | Gunatillake et al. | |
| 6,863,685 B2 * | 3/2005 | Davila et al. | 623/1.34 |
| 6,867,389 B2 | 3/2005 | Shapovalov et al. | |
| 6,878,758 B2 | 4/2005 | Martin et al. | |
| 6,891,126 B2 | 5/2005 | Matile | |
| 6,899,729 B1 | 5/2005 | Cox et al. | |
| 6,911,041 B1 | 6/2005 | Zscheeg | |
| 6,913,762 B2 | 7/2005 | Caplice et al. | |
| 6,918,928 B2 | 7/2005 | Wolinsky et al. | |
| 6,926,733 B2 | 8/2005 | Stinson | |
| 6,943,964 B1 | 9/2005 | Zhang et al. | |
| 6,981,982 B2 | 1/2006 | Armstrong et al. | |
| 6,981,987 B2 | 1/2006 | Huxel et al. | |
| 7,022,132 B2 | 4/2006 | Kocur | |
| 7,128,737 B1 | 10/2006 | Goder et al. | |
| 7,163,555 B2 | 1/2007 | Dinh | |
| 7,166,099 B2 | 1/2007 | Devens, Jr. | |
| 7,226,475 B2 | 6/2007 | Lenz et al. | |
| 7,243,408 B2 * | 7/2007 | Vietmeier | 29/447 |
| 7,326,245 B2 | 2/2008 | Rosenthal et al. | |
| 7,331,986 B2 | 2/2008 | Brown et al. | |
| 7,500,988 B1 | 3/2009 | Butaric et al. | |
| 7,776,926 B1 | 8/2010 | Hossainy et al. | |
| 2001/0001317 A1 | 5/2001 | Duerig et al. | |
| 2001/0021871 A1 | 9/2001 | Stinson | |
| 2001/0021873 A1 * | 9/2001 | Stinson | 623/1.34 |
| 2001/0027339 A1 | 10/2001 | Boatman et al. | |
| 2001/0029398 A1 | 10/2001 | Jadhav | |
| 2001/0044652 A1 | 11/2001 | Moore | |
| 2002/0002399 A1 | 1/2002 | Huxel et al. | |
| 2002/0004060 A1 | 1/2002 | Heublein et al. | |
| 2002/0004101 A1 | 1/2002 | Ding et al. | |
| 2002/0032486 A1 | 3/2002 | Lazarovitz et al. | |
| 2002/0062148 A1 | 5/2002 | Hart | |
| 2002/0065553 A1 | 5/2002 | Weber | |
| 2002/0103528 A1 | 8/2002 | Schaldach et al. | |
| 2002/0111590 A1 | 8/2002 | Davila et al. | |
| 2002/0116050 A1 | 8/2002 | Kocur | |
| 2002/0138133 A1 | 9/2002 | Lenz et al. | |
| 2002/0143386 A1 | 10/2002 | Davila et al. | |
| 2002/0161114 A1 | 10/2002 | Gunatillake et al. | |
| 2002/0190038 A1 | 12/2002 | Lawson | |
| 2002/0193862 A1 | 12/2002 | Mitelberg et al. | |
| 2003/0004563 A1 | 1/2003 | Jackson et al. | |
| 2003/0028241 A1 | 2/2003 | Stinson | |
| 2003/0028245 A1 | 2/2003 | Barclay et al. | |
| 2003/0033001 A1 | 2/2003 | Igaki | |
| 2003/0039689 A1 | 2/2003 | Chen et al. | |
| 2003/0050688 A1 | 3/2003 | Fischell et al. | |
| 2003/0060872 A1 | 3/2003 | Gomringer et al. | |
| 2003/0065355 A1 | 4/2003 | Weber | |
| 2003/0069630 A1 * | 4/2003 | Burgermeister et al. | 623/1.15 |
| 2003/0093107 A1 | 5/2003 | Parsonage et al. | |
| 2003/0100865 A1 | 5/2003 | Santini, Jr. et al. | |
| 2003/0105518 A1 | 6/2003 | Dutta | |
| 2003/0105530 A1 | 6/2003 | Pirhonen | |
| 2003/0108588 A1 | 6/2003 | Chen | |
| 2003/0121148 A1 | 7/2003 | DiCaprio | |
| 2003/0153971 A1 | 8/2003 | Chandrasekaran | |
| 2003/0155328 A1 | 8/2003 | Huth et al. | |
| 2003/0171053 A1 | 9/2003 | Sanders | |
| 2003/0187495 A1 | 10/2003 | Cully et al. | |
| 2003/0208259 A1 | 11/2003 | Penhasi | |
| 2003/0209835 A1 | 11/2003 | Chun et al. | |
| 2003/0226833 A1 | 12/2003 | Shapovalov et al. | |
| 2003/0236565 A1 | 12/2003 | DiMatteo et al. | |
| 2004/0015228 A1 | 1/2004 | Lombardi et al. | |
| 2004/0044399 A1 | 3/2004 | Ventura | |
| 2004/0073291 A1 | 4/2004 | Brown et al. | |
| 2004/0088039 A1 | 5/2004 | Lee et al. | |
| 2004/0093077 A1 | 5/2004 | White et al. | |
| 2004/0098090 A1 | 5/2004 | Williams et al. | |
| 2004/0098095 A1 | 5/2004 | Burnside et al. | |
| 2004/0106987 A1 | 6/2004 | Palasis et al. | |
| 2004/0111149 A1 | 6/2004 | Stinson | |
| 2004/0122509 A1 | 6/2004 | Brodeur | |
| 2004/0126405 A1 | 7/2004 | Sahatjian | |
| 2004/0127970 A1 | 7/2004 | Saunders et al. | |
| 2004/0143180 A1 | 7/2004 | Zhong et al. | |
| 2004/0143317 A1 | 7/2004 | Stinson et al. | |
| 2004/0167610 A1 | 8/2004 | Fleming, III | |
| 2004/0167619 A1 | 8/2004 | Case et al. | |
| 2004/0181236 A1 | 9/2004 | Eidenschink et al. | |
| 2004/0204750 A1 | 10/2004 | Dinh | |
| 2004/0220662 A1 * | 11/2004 | Dang et al. | 623/1.16 |
| 2004/0236428 A1 | 11/2004 | Burkinshaw et al. | |
| 2005/0004653 A1 | 1/2005 | Gerberding et al. | |
| 2005/0004663 A1 | 1/2005 | Llanos et al. | |
| 2005/0015138 A1 | 1/2005 | Schuessler et al. | |
| 2005/0021131 A1 | 1/2005 | Venkatraman et al. | |
| 2005/0060025 A1 | 3/2005 | Mackiewicz et al. | |
| 2005/0087520 A1 | 4/2005 | Wang et al. | |
| 2005/0107865 A1 | 5/2005 | Clifford et al. | |
| 2005/0111500 A1 | 5/2005 | Harter et al. | |
| 2005/0147647 A1 | 7/2005 | Glauser et al. | |
| 2005/0154450 A1 | 7/2005 | Larson et al. | |
| 2005/0157382 A1 | 7/2005 | Kafka et al. | |
| 2005/0172471 A1 * | 8/2005 | Vietmeier | 29/447 |
| 2005/0211680 A1 | 9/2005 | Li et al. | |
| 2005/0283226 A1 | 12/2005 | Haverkost | |
| 2005/0283228 A1 | 12/2005 | Stanford | |
| 2006/0025847 A1 | 2/2006 | Parker | |
| 2006/0033240 A1 | 2/2006 | Weber et al. | |
| 2006/0120418 A1 | 6/2006 | Harter et al. | |
| 2006/0173528 A1 | 8/2006 | Feld et al. | |
| 2006/0241741 A1 | 10/2006 | Lootz | |
| 2007/0156230 A1 * | 7/2007 | Dugan et al. | 623/1.16 |
| 2007/0266542 A1 | 11/2007 | Melsheimer | |
| 2008/0009938 A1 | 1/2008 | Huang et al. | |
| 2008/0015684 A1 | 1/2008 | Wu | |
| 2008/0033532 A1 | 2/2008 | Dave | |
| 2008/0188924 A1 | 8/2008 | Prabhu | |
| 2009/0076594 A1 | 3/2009 | Sabaria | |
| 2009/0204203 A1 | 8/2009 | Allen et al. | |
| 2013/0150943 A1 | 6/2013 | Zheng et al. | |
| 2013/0325104 A1 | 12/2013 | Wu | |
| 2013/0325105 A1 | 12/2013 | Wu | |
| 2013/0325107 A1 | 12/2013 | Wu | |
| 2013/0331926 A1 | 12/2013 | Wu | |

FOREIGN PATENT DOCUMENTS

| | | |
|---|---|---|
| DE | 103 61942 | 7/2005 |
| DE | 10 2004 045994 | 3/2006 |
| EP | 0583170 | 2/1994 |
| EP | 0714641 | 6/1996 |
| EP | 0842729 | 5/1998 |
| EP | 1210 922 | 6/2002 |
| EP | 1 591 079 | 11/2005 |
| EP | 1 656 905 | 5/2006 |
| JP | 4-33791 | 2/1992 |
| JP | 7-124766 | 5/1995 |
| JP | 10-166156 | 6/1998 |
| JP | 2003-53577 | 2/2003 |
| WO | WO 95/27587 | 10/1995 |
| WO | WO 99/20429 | 4/1999 |
| WO | WO 02/26162 | 4/2002 |

(56) References Cited

FOREIGN PATENT DOCUMENTS

| WO | WO 02/38325 | 5/2002 |
|---|---|---|
| WO | WO 03/015978 | 2/2003 |
| WO | WO 03/057075 | 7/2003 |
| WO | WO 2004/019820 | 3/2004 |
| WO | WO 2004/062533 | 7/2004 |
| WO | WO 2004/112863 | 12/2004 |
| WO | WO 2005/023480 | 3/2005 |
| WO | WO 2007/081551 | 7/2007 |

OTHER PUBLICATIONS

Fan et al., *Plasma Absorption of Femtosecond Laser Pulses in Dielectrics*, J. of Heat Transfer, vol. 124, pp. 275-283 (2002).

Feng-Chun et al., *Assessment of Tissue Blood Flow Following Small Artery Welding with an Intraluminal Dissolvable Stent*, Microsurgery, vol. 19(3), pp. 148-152 (1999).

Hoffnagle et al., *Design and performance of a refractive optical system that converts a Gaussian to a flattop beam*, Applied Optics, vol. 39, No. 30 pp. 5488-5499 (2000).

International Search Rep. for PCT/US2007/015561 filed Jul. 6, 2007, mailed Dec. 4, 2007, 7 pgs.

International Search Report for PCT/US2006/049269, filed Dec. 21, 2006, mailed Jun. 15, 2007, 19 pgs.

Sun et al., "Inert gas beam delivery for ultrafast laser micromachining at ambient pressure", Am. Inst. of Physics, 6 pgs.

Zhang et al., "Single-element laser beam shaper for uniform flat-top profiles" Optics Express, vol. 11, No. 16, pp. 1942-1948 (2003).

U.S. Appl. No. 11/009,977, Pacetti, filed Dec. 9, 2004.

U.S. Appl. No. 11/325,974, Dugan et al., filed Jan. 4, 2006.

U.S. Appl. No. 12/172,020, Wang, filed Jul. 11, 2008.

\* cited by examiner

METHOD OF MAKING STENTS WITH RADIOPAQUE MARKERS

CROSS REFERENCE TO RELATED APPLICATION

This is a continuation of application Ser. No. 11/796,226, filed on Apr. 26, 2007 which in turned claims benefit of provisional application No. 60/809,088, filed on May 26, 2006, both of which is still pending and are incorporated herein by reference in their entirety.

BACKGROUND OF THE INVENTION

1. Field of the Invention

This invention relates to implantable medical devices, such as stents. In particular, the invention relates to polymeric stents with radiopaque markers.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopaque" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be radiopaque, or fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials may be configured to meet this additional clinical requirement since they may be designed to completely erode after the clinical need for them has ended. Stents fabricated from biodegradable polymers are particularly promising, in part because they may be designed to completely erode within a desired time frame.

However, a significant shortcoming of biodegradable polymers (and polymers generally composed of carbon, hydrogen, oxygen, and nitrogen) is that they are radiolucent with no radiopacity. Biodegradable polymers tend to have x-ray absorption similar to body tissue.

One way of addressing this problem is to attach or couple radiopaque markers to a stent. The radiopaque markers allow the position of the stent to be monitored since the markers are can be imaged by X-ray imaging techniques. The ability to monitor or detect a stent visually is limited by the visibility of the markers.

SUMMARY OF THE INVENTION

Various embodiments of the present invention include a stent comprising radiopaque markers disposed on or within the stent, wherein the radiopaque markers are arranged longitudinally along an axis of the stent.

Further embodiments of the present invention include a stent comprising radiopaque markers disposed on or within the stent, wherein the radiopaque markers are arranged in a pattern along the circumference of the stent.

Additional embodiments of the present invention include a stent comprising a plurality of radiopaque markers disposed on or within on the stent, wherein the plurality of radiopaque markers are selectively arranged in a region of the stent to enhance the visibility of the stent with an imaging technique.

DETAILED DESCRIPTION OF THE INVENTION

The present invention may be applied to stents and, more generally, implantable medical devices such as, but not limited to, self-expandable stents, balloon-expandable stents, stent-grafts, vascular grafts, cerebrospinal fluid shunts, pacemaker leads, closure devices for patent foramen ovale, and synthetic heart valves.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. A polymeric wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Figure 1:
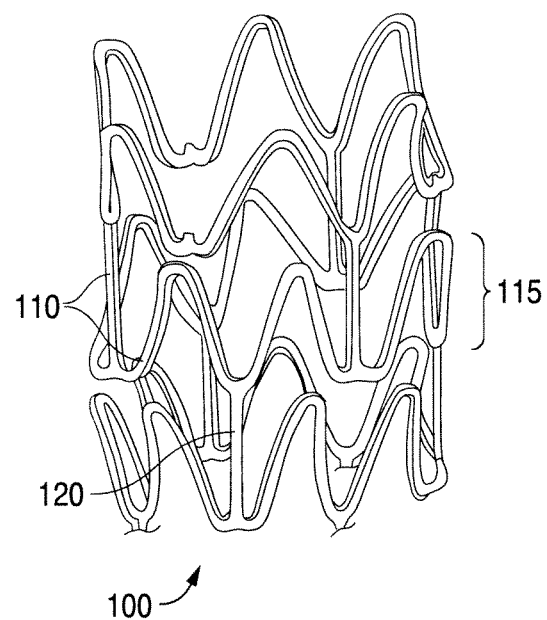
FIG. 1 depicts an exemplary stent.

FIG. 1 depicts an exemplary stent 100 with struts 110 that form cylindrical rings 115 which are connected by linking struts 120. The cross-section of the struts in stent 100 are rectangular-shaped. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

A stent can be made of a biostable and/or biodegradable polymer. As indicated above, a stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration can be in a range from about a month to a few years. However, the duration is typically in a range from about one month to twelve months, or in some embodiments, six to twelve months. It is important for the stent to provide mechanical support to a vessel for at least a portion of the duration. Many biodegradable polymers have erosion rates that make them suitable for treatments that require the presence of a device in a vessel for the above-mentioned time-frames.

As indicated above, it is desirable to have the capability of obtaining images of polymeric stents with x-ray fluoroscopy during and after implantation. Various embodiments of the present invention include stents with markers arranged in patterns or selectively arranged on the stent in a manner that facilitates visualization of the stent.

Various types of markers can be used in embodiments of the present invention. Representative types of markers include constructs made of a radiopaque material that is disposed within depots or holes in a stent. The construct can be, but is not limited to a pellet, bead, or slug. The depot or hole can be made to accommodate the shape of the marker. In an embodiment, the depot may be formed in a structural element by laser machining. The depot may extend partially or completely through the portion of the stent. For example, an opening of a depot may be on an abluminal or luminal surface and extend partially through the stent or completely through to an opposing surface. The markers may be sufficiently radiopaque for imaging the stent. In addition, embodiments of the stents with markers should be biocompatible and should not interfere with treatment.

Figure 2:
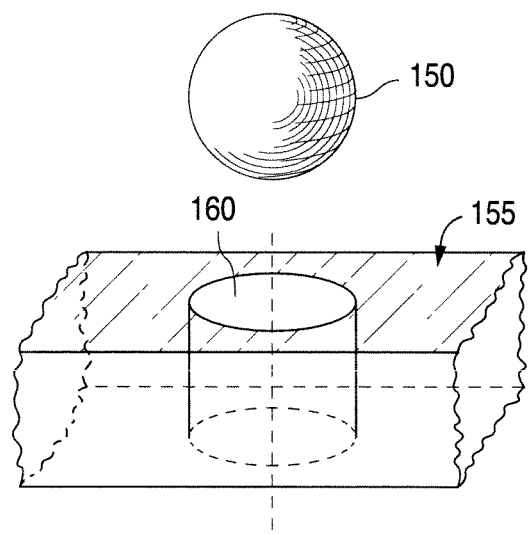
FIG. 2 depicts an exemplary embodiment of a radiopaque marker and a section of a structural element of a stent with a depot for receiving the marker.

FIG. 2 illustrates an exemplary embodiment of a spherical marker 150 and a section 155 of a structural element of a stent with a cylindrical depot 160. Depot 160 accommodates the shape of spherical marker 150 so that is can be positioned within depot 160. Markers can be attached or coupled to a stent using various techniques, including, but not limited to, gluing, welding, or through an interference fit.

The markers and manner of positioning on the stent are merely representative. Embodiments of the present invention are not limited to the type of marker or the manner of attachment or coupling to the stent. The present invention applies to markers that can be attached or coupled in, on, or around a stent at a specific locations or positions on the stent structure or geometry.

In general, increasing the size of a marker enhances the visibility of a stent. However, increasing the size of a marker can have disadvantages. For example, a larger marker can result in an undesirably large profile of the stent which can interfere with the flow of blood in a vessel. Complications such as thrombosis can result from the disturbed blood flow. Additionally, a larger marker disposed in a structural element can negatively affect its structural integrity.

Embodiments of the present invention are directed to positioning or arranging markers on a stent to facilitate detection or monitoring the position of the stent. In certain embodiments, the markers can be arranged in a geometrical pattern that facilitates visualization of the stent.

Figure 3:
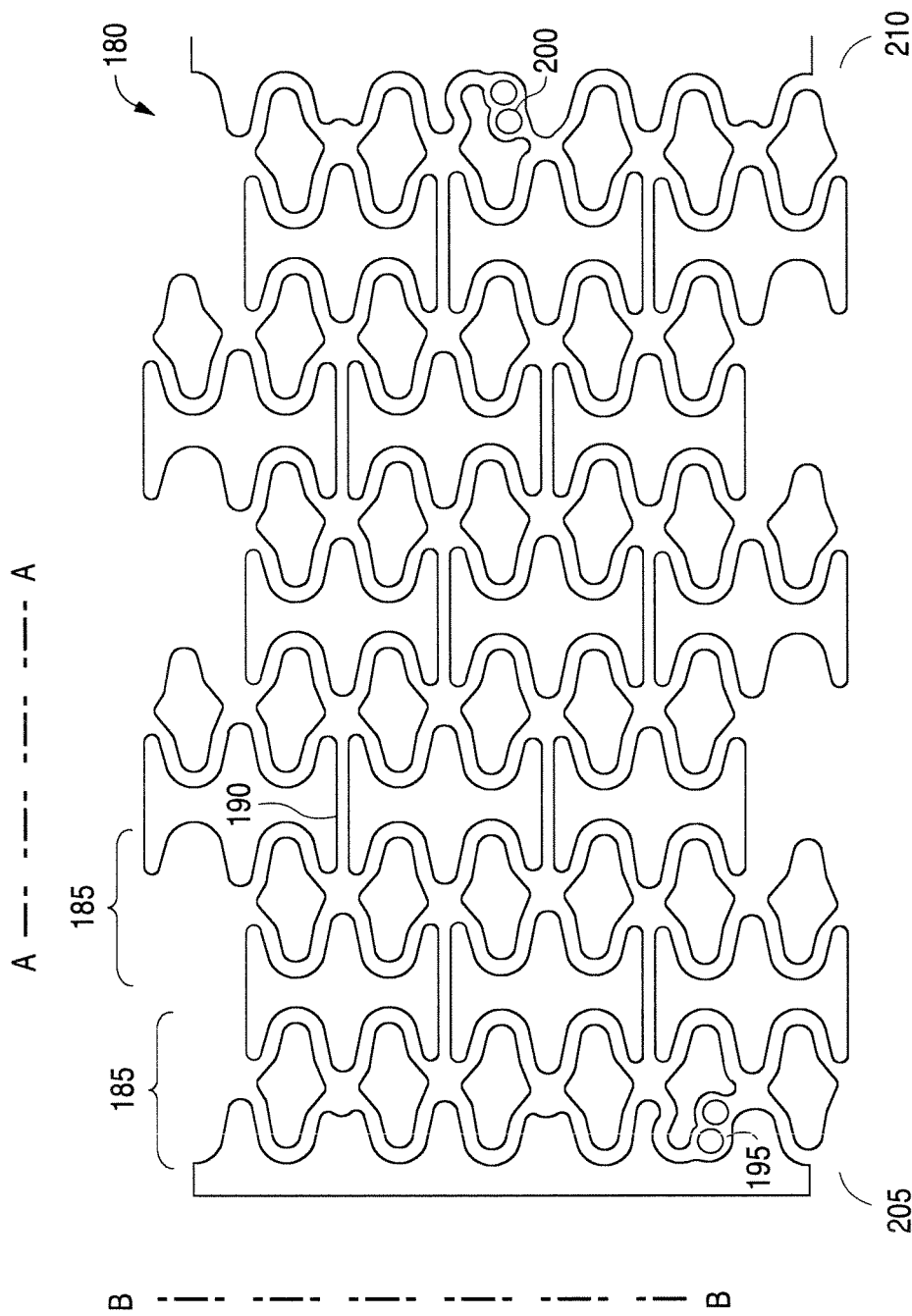
FIG. 3 depicts a stent pattern with radiopaque markers at proximal and distal ends.

FIG. 3 depicts a stent pattern 180 in a flattened condition showing an abluminal or luminal surface so that the pattern can be clearly viewed. When the flattened portion of stent pattern 180 is in a cylindrical condition, it forms a radially expandable stent. Line A-A corresponds to the longitudinal axis of a stent made from stent pattern 180 and line B-B corresponds to the circumferential direction of a stent made from stent pattern 180.

Stent pattern 180 includes cylindrically aligned rings 185 and linking structural elements 190. Structural elements at a proximal end 205 and distal end 210 of stent pattern 180 include depots with pairs of radiopaque markers 195 and 200, respectively, disposed within the depots. As shown FIG. 3, the structural elements are thicker in the vicinity of markers 195 and 200 to compensate for the presence of the depots. In general, it is desirable to place radiopaque markers in regions of a stent pattern that experience relatively low strain during crimping and expansion. Such low strain regions include straight portions of structural elements and "spider regions" which are intersections of three or more structural elements.

A physician can monitor the position of the stent due to the presence of the radiopaque markers which are visible using X-ray imaging. Since markers are located at the distal and proximal ends of the stent, the positions of the markers allow the physician to locate the ends of the stent. However, the small size of the markers can make it difficult to visually detect the individual markers. As indicated above, the size of markers is limited by a desired profile of the stent and structural integrity of structural elements. Since the markers are separated by the length of the stent, locating the ends of the stent can be difficult.

Various embodiments of the present invention include a stent having radiopaque markers arranged in patterns or selectively arranged in a region in a manner that enhances or facilitates visualization of the stent. Radiopaque markers arranged in patterns or selectively arranged in particular region(s) have greater visibility than one or two localized markers and can substantially enhance the visibility of a stent.

Figure 4:
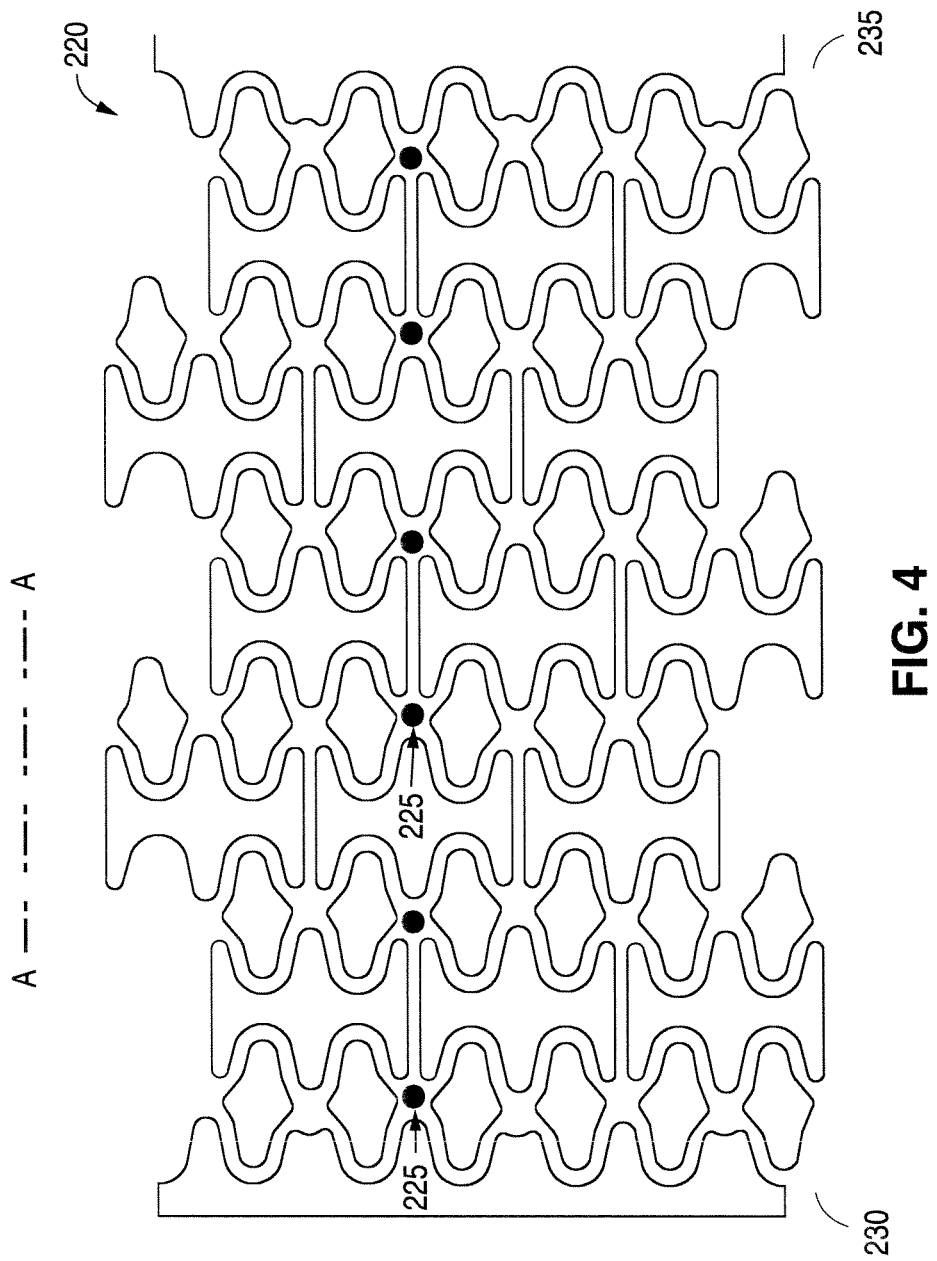
FIG. 4 depicts a stent pattern with radiopaque markers arranged longitudinally along the cylindrical axis.

FIG. 4 depicts an exemplary stent pattern 220 of the present invention. Stent pattern 220 is the same as pattern 180 in FIG. 3 except for the number and arrangement of radiopaque markers. Stent pattern 220 includes radiopaque markers 225 which are arranged longitudinally along the cylindrical axis of stent pattern 220. Radiopaque markers 225 can be placed in or on any portion of the structural elements of stent pattern 220, as long as the mechanical integrity of the structural element is not undesirably compromised. As shown in FIG. 4, radiopaque markers 220 are located in the "spider regions," which are relatively low strain regions of stent pattern 220. Such a pattern is substantially more visible than one or two markers localized at either end of the stent, as depicted in FIG. 3.

The longitudinal pattern of markers 225 extends from a proximal end 230 to a distal end 235 of stent pattern 220. In some embodiments, the pattern does not extend all the way between the proximal end and distal end. A portion between the proximal and distal ends can be devoid of markers.

Figure 5:
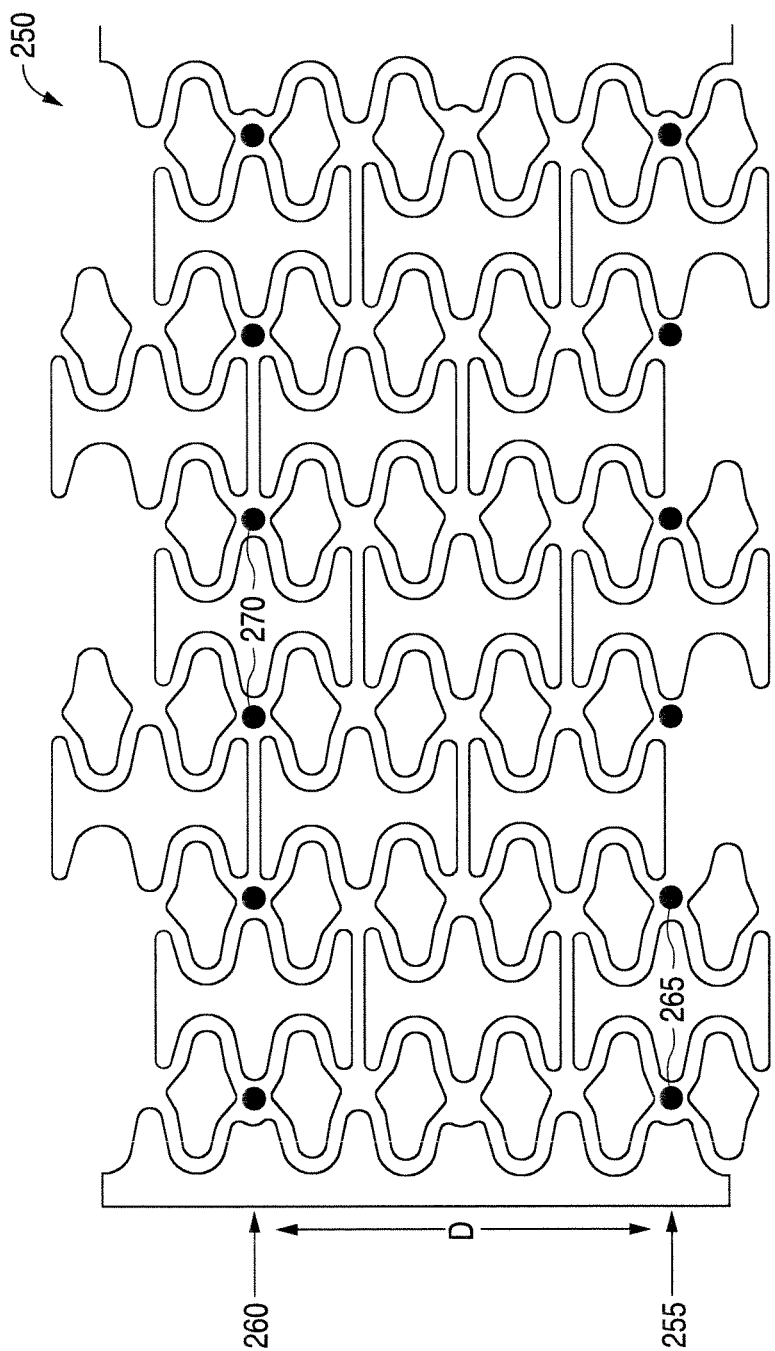
FIG. 5 depicts a stent pattern with radiopaque markers arranged in two longitudinally patterns along the cylindrical axis.

In other embodiments, the visibility of the stent can be further enhanced by including additional marker patterns. For example, FIG. 5 depicts another exemplary stent pattern 250 of the present invention that is the same as the stent patterns of FIGS. 3 and 4 except for the number and arrangement of radiopaque markers. Stent pattern 250 includes a longitudinal pattern 255 of markers 265 and another longitudinal pattern 260 of markers 270 at a different circumferential position. Marker patterns 255 and 260 are separated by a circumferential distance or arc D. D can be between 0° and 45°, 45° and 90°, 90° and 135°, and between 135 and 180°.

Figure 6:
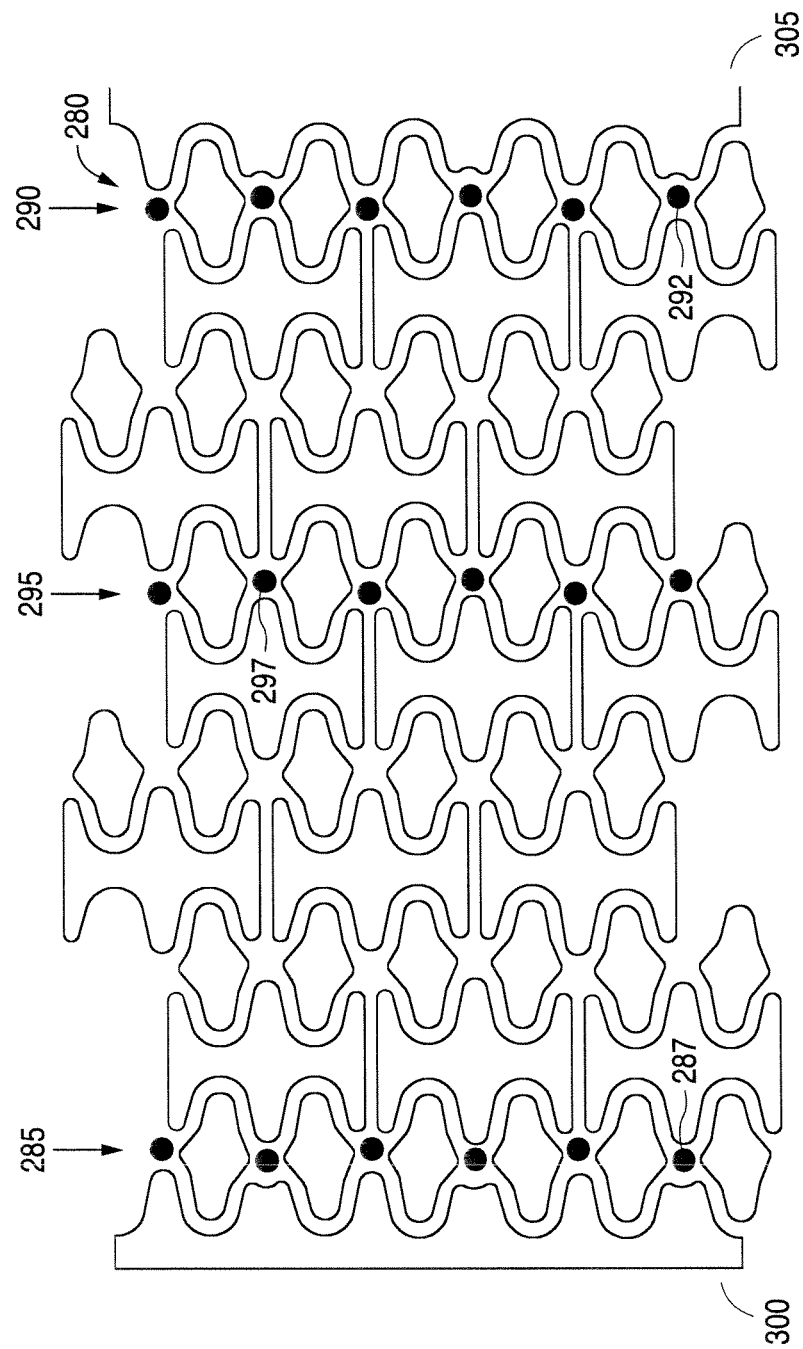
FIG. 6 depicts a stent pattern with radiopaque markers arranged in circumferential patterns.

Further embodiments can include marker patterns along at least a portion of the circumference. Such marker patterns can include, but are not limited to, a circular pattern, diagonal pattern, or a spiral pattern. FIG. 6 depicts another exemplary stent pattern 280 of the present invention that is the same as the previous stent patterns except for the number and arrangement of radiopaque markers. Stent pattern 280 includes three circumferential marker patterns: a marker pattern 285 with markers 287 at a proximal end 300, a marker pattern 290 with markers 292 at a distal end 305, and a marker pattern 295 with markers 297 between proximal end 300 and distal end 305. These marker patterns substantially enhance the visibility of the ends of the stent as compared to one or two markers at the ends, such as that illustrated in FIG. 3.

Figure 7:
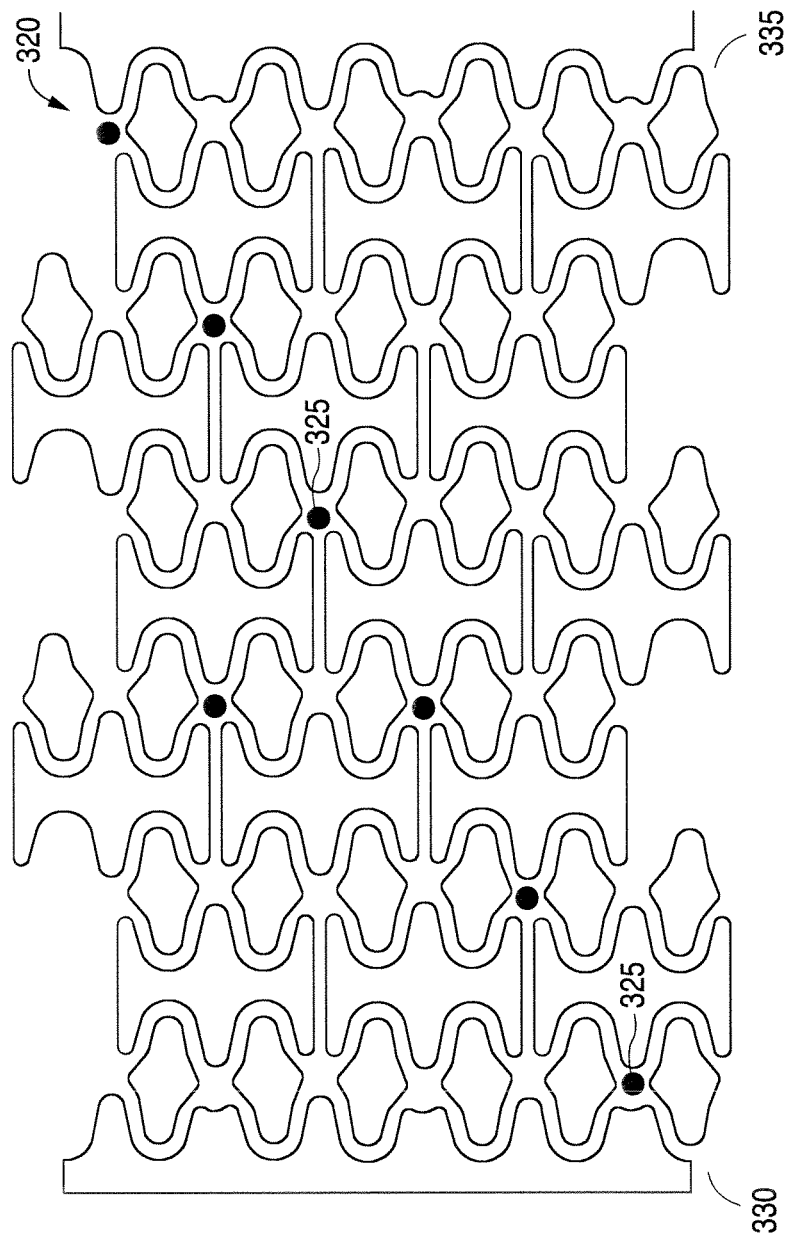
FIG. 7 depicts a stent pattern with radiopaque markers arranged in a diagonal pattern.

Each of the circumferential patterns extends all the way around the circumference of a stent made from stent pattern 280 and is positioned at a single axial position. Alternatively, the circumferential patterns can extend partially around the circumference. Circumferential patterns can also extend diagonally around the circumference so that the marker pattern is not a single axial position. For example, FIG. 7 depicts an exemplary stent pattern 320 that has a diagonal marker pattern with markers 325 extending between a proximal end 330 to a distal end 335.

Figure 8:
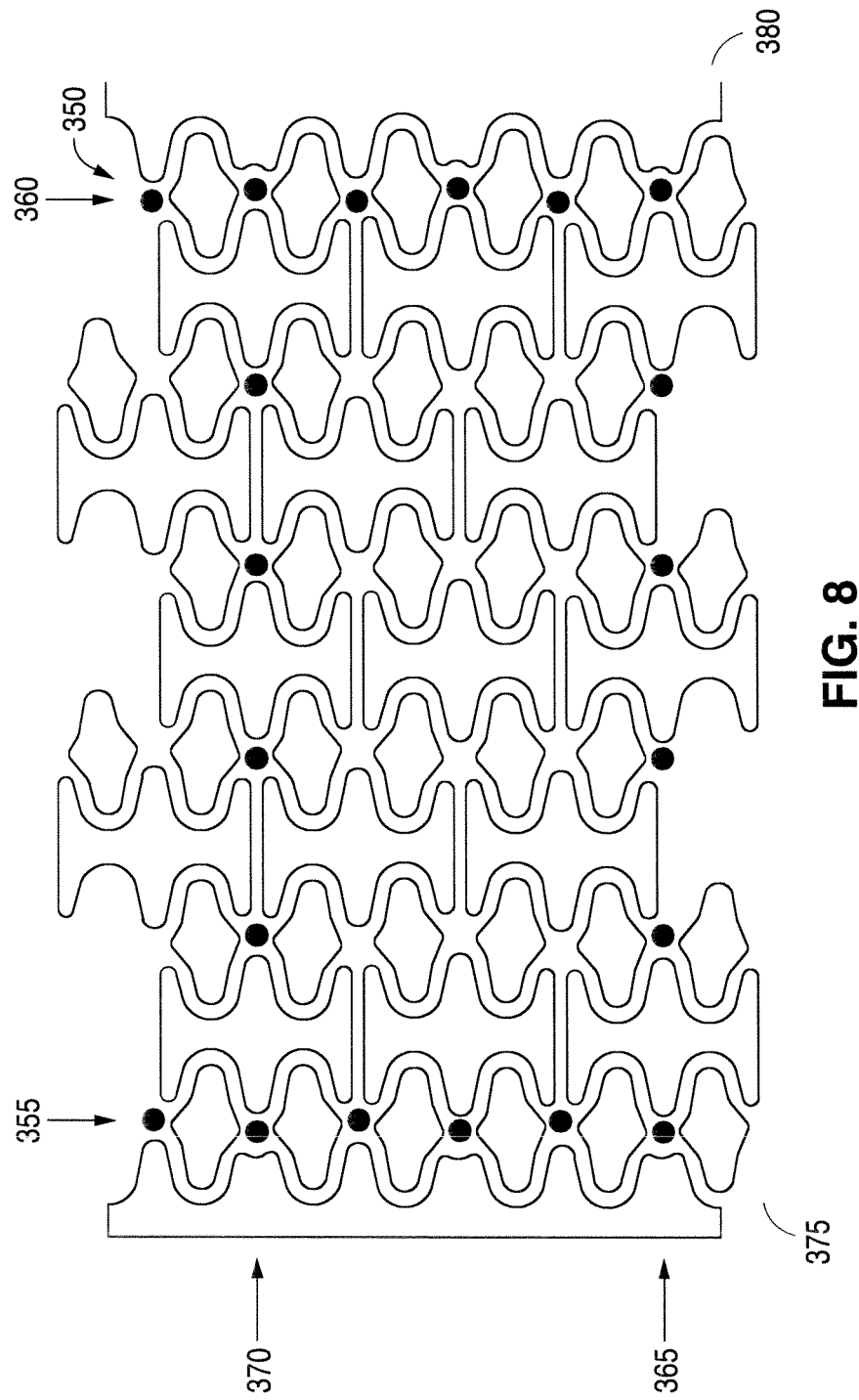
FIG. 8 depicts a stent pattern with radiopaque markers arranged in circumferential patterns and longitudinal patterns.

In some embodiments, a stent can include both longitudinal and circumferential marker patters. FIG. 8 depicts an exemplary stent pattern 350 of the present invention that is the same as the previous stent patterns except for the number and arrangement of radiopaque markers. Stent pattern 350 includes two circumferential marker patterns, 355 and 360, and two longitudinal marker patterns, 365 and 370. Marker patterns 355 and 360 are at proximal end 375 and 380. Such a combination of patterns enhances the visibility of both the ends of the stent as well as the longitudinal extent of the stent.

Figure 9:
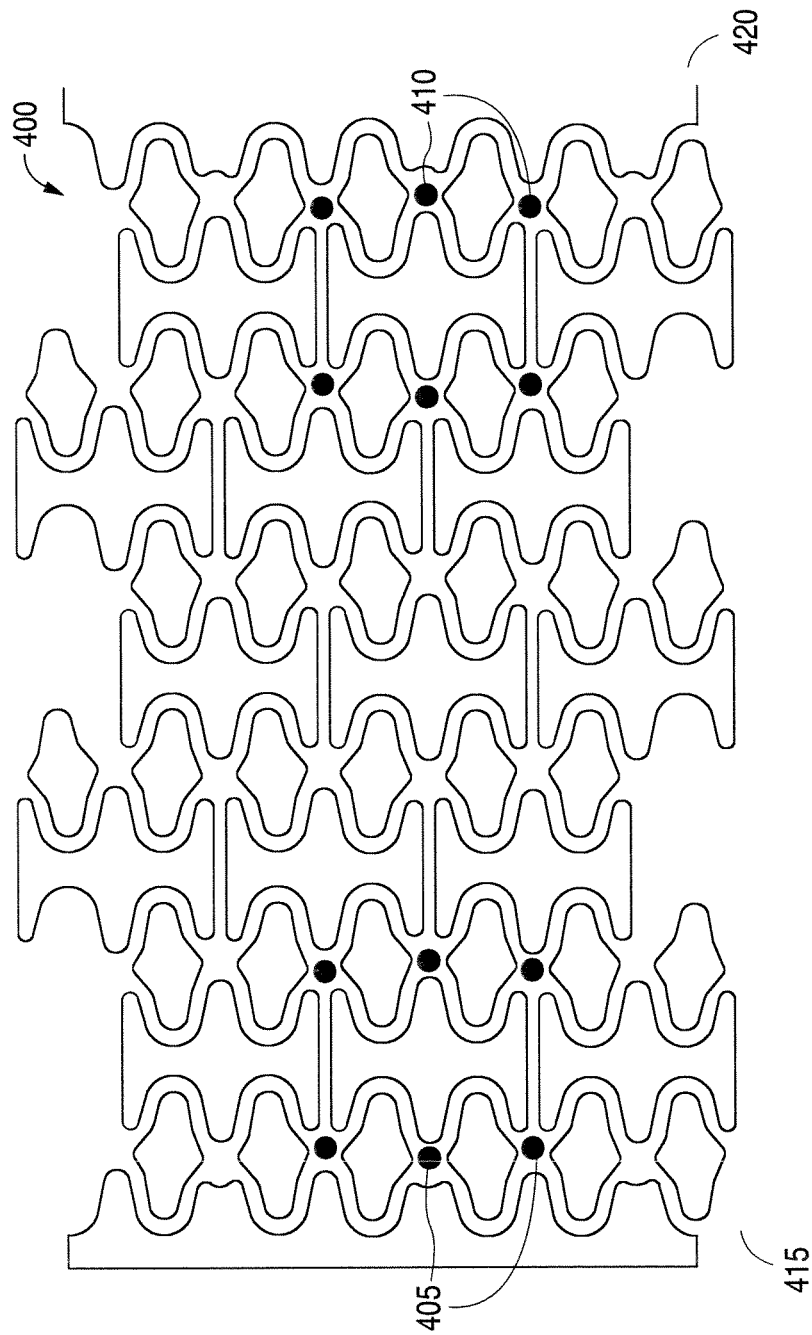
FIG. 9 depicts a stent pattern with radiopaque markers selectively arranged in the proximal and distal regions of a stent.

In certain embodiments, a plurality of radiopaque markers can be selectively arranged in a region of the stent to enhance the visibility of the stent with an imaging technique. For example, the markers can be selectively arranged at a proximal region, distal region, or both. FIG. 9 depicts an exemplary stent pattern 400 of the present invention that is the same as the previous stent patterns except for the number and arrangement of radiopaque markers. Stent pattern 400 includes a group of markers 405 arranged at a proximal end 415 and a group of markers 410 arranged at a distal end 420. The groups of markers tend to increase the visibility of the respective ends of the stent as compared to the markers is FIG. 3. The individual markers can be selected and coupled in a way that there is little or no negative effect on the structural integrity of the stent and also with a relatively low profile.

As indicated above, a stent may have regions with a lower strain than other higher strain regions when the stent is placed under an applied stress during use. A depot for a radiopaque marker may be selectively positioned in a region of lower strain. The selected region of the structural element may be modified to have a higher mass or thickness than a region of lower strain without a marker so as to maintain the load-bearing capability of the region and to inhibit decoupling of the marker from the stent.

Furthermore, the markers may be coupled to any desired location on a stent. In some embodiments, it may be advantageous to limit the placement of a marker to particular locations or portions of surfaces of a stent. For example, it may be desirable to couple a marker at a sidewall face of a structural element to reduce or eliminate interference with a lumen wall or interference with blood flow, respectively. To delineate just the margins of the stent so that the physician may see its full length, markers can be placed only at the distal and proximal ends of the stent.

As indicated above, a stent may include a biostable and/or a biodegradable polymer. The biodegradable polymer may be a pure or substantially pure biodegradable polymer. Alternatively, the biodegradable polymer may be a mixture of at least two types of biodegradable polymers. The stent may be configured to completely erode away once its function is fulfilled.

In certain embodiments, the marker may be biodegradable. It may be desirable for the marker to degrade at the same or substantially the same rate as the stent. For instance, the marker may be configured to completely or almost completely erode at the same time or approximately the same time as the stent. In other embodiments, the marker may degrade at a faster rate than the stent. In this case, the marker may completely or almost completely erode before the body of the stent is completely eroded.

Furthermore, a radiopaque marker may be composed of a biodegradable and/or biostable metal. Biodegradable or bioerodable metals tend to erode or corrode relatively rapidly when exposed to bodily fluids. Biostable metals refer to metals that are not biodegradable or bioerodable or have negligible erosion or corrosion rates when exposed to bodily fluids. Additionally, it is desirable to use a biocompatible biodegradable metal for a marker. A biocompatible biodegradable metal forms erosion products that do not negatively impact bodily functions.

In one embodiment, a radiopaque marker may be composed of a pure or substantially pure biodegradable metal. Alternatively, the marker may be a mixture or alloy of at least two types of metals. Representative examples of biodegradable metals for use in a marker may include, but are not limited to, magnesium, zinc, tungsten, and iron. Representative mixtures or alloys may include magnesium/zinc, magnesium/iron, zinc/iron, and magnesium/zinc/iron. Radiopaque compounds such as iodine salts, bismuth salts, or barium salts may be compounded into the metallic biodegradable marker to further enhance the radiopacity. Representative examples of biostable metals can include, but are not limited to, platinum and gold.

In some embodiments, the composition of the marker may be modified or tuned to obtain a desired erosion rate and/or degree of radiopacity. For example, the erosion rate of the marker may be increased by increasing the fraction of a faster eroding component in an alloy. Similarly, the degree of radiopacity may be increased by increasing the fraction of a more radiopaque metal, such as iron, in an alloy. In one embodiment, a biodegradable marker may be completely eroded when exposed to bodily fluids, such as blood, between about a week and about three months, or more narrowly, between about one month and about two months.

In other embodiments, a radiopaque marker may be a mixture of a biodegradable polymer and a radiopaque material. A radiopaque material may be biodegradable and/or bioabsorbable. Representative radiopaque materials may include, but are not limited to, biodegradable metallic particles and particles of biodegradable metallic compounds such as biodegradable metallic oxides, biocompatible metallic salts, gadolinium salts, and iodinated contrast agents.

In some embodiments, the radiopacity of the marker may be increased by increasing the composition of the radiopaque material in the marker. In one embodiment, the radiopaque material may be between 10% and 80%; 20% and 70%; 30% and 60%; or 40% and 50% by volume of the marker.

The biodegradable polymer in the marker may be a pure or substantially pure biodegradable polymer. Alternatively, the biodegradable polymer may be a mixture of at least two types of biodegradable polymers. In one embodiment, the composition of the biodegradable polymer may be modified to alter the erosion rate of the marker since different biodegradable polymers have different erosion rates.

A biocompatible metallic salt refers to a salt that may be safely absorbed by a body. Representative biocompatible metallic salts that may used in a marker include, but are not limited to, ferrous sulfate, ferrous gluconate, ferrous carbonate, ferrous chloride, ferrous fumarate, ferrous iodide, ferrous lactate, ferrous succinate, barium sulfate, bismuth subcarbonate, bismuth potassium tartrate, bismuth sodium iodide, bismuth sodium tartrate, bismuth sodium triglycollamate, bismuth subsalicylate, zinc acetate, zinc carbonate, zinc citrate, zinc iodate, zinc iodide, zinc lactate, zinc phosphate, zinc salicylate, zinc stearate, zinc sulfate, and combinations thereof. The concentration of the metallic salt in the marker may be between 10% and 80%; 20% and 70%; 30% and 60%; or 40% and 50% by volume of the marker.

In addition, representative iodinated contrast agents may include, but are not limited to acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. The concentration of an iodinated contrast agent in the marker may be between 5% and 80%; 20% and 70%; 30% and 60%; or 40% and 50% by volume of the marker.

The composition of metallic particles may include at least those biodegradable metals discussed above as well as metallic compounds such as oxides. The concentration of metallic particles in the marker may be between 10% and 80%; 20% and 70%; 30% and 60%; or 40% and 50% by volume of the marker. Additionally, individual metallic particles may be a pure or substantially pure metal or a metal compound. Alternatively, individual metallic particles may be a mixture of at least two types of metals or metallic compounds. Individual metallic particles may also be a mixture or an alloy composed of at least two types of metals.

In certain embodiments, the metallic particles may be metallic nanoparticles. A "nanoparticle" refers to a particle with a dimension in the range of about 1 nm to about 100 nm. A significant advantage of nanoparticles over larger particles is that nanoparticles may disperse more uniformly in a polymeric matrix, which results in more uniform properties such as radiopacity and erosion rate. Additionally, nanoparticles may be more easily absorbed by bodily fluids such as blood without negative impact to bodily functions. Representative examples of metallic particles may include, but are not limited to, iron, magnesium, zinc, platinum, gold, tungsten, and oxides of such metals.

In one embodiment, the composition of different types of metallic particles in the mixture as well as the composition of individual particles may be modified to alter erosion rates and/or radiopacity of the marker. In addition, the ratio of polymer to metallic particles may be modified to alter both the erosion rate, and radiopacity.

A marker may be fabricated by methods including, but not limited to, molding, machining, assembly, or a combination thereof. All or part of a metallic or polymeric marker may be fabricated in a mold or machined by a method such as laser machining.

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel. The decrease in molecular weight may be caused by, for example, hydrolysis, oxidation, enzymolysis, and/or metabolic processes.

Representative examples of polymers that may be used to fabricate embodiments of stents, or more generally, implantable medical devices include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alpha-olefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of crimping a stent on a balloon, comprising:
    (a) providing a biodegradable polymeric stent, wherein the material from which structural elements of the stent are made consist of poly(l-lactide) and a second, different polymer ("PLLA-based polymer");
    (b) attaching markers to the polymeric stent to provide capability of obtaining images of the PLLA-based polymer stent with an imaging device during and after implantation of the stent in a vessel,
    wherein the stent consists of two pairs of markers, two of the markers being attached in an adjacent configuration about a proximal most end ring of the stent, and the remaining two markers being attached in an adjacent configuration about a distal most end ring of the stent, with the proviso that the stent has no other markers but for the four markers to allow for imaging of the PLLA-based polymer stent and with a further proviso that an entire length of the stent between the first pair and second pair of markers is devoid of any markers,
    wherein a center point of a first marker is positioned at a circumferential distance from a center point of its adjacent second marker,
    wherein a center point of a third marker is positioned at a circumferential distance from a center point of its adjacent fourth marker, and
    wherein the pair of markers about the proximal most end ring of the polymeric stent are circumferentially off-set from the pair of markers about the distal most end ring of the polymeric stent; and
    (c) crimping the stent on a balloon of a catheter assembly by application of a crimping pressure to the stent positioned over the balloon,
    wherein when the crimping pressure is applied to the stent, the stent has regions of low strain and regions of high strain, such that PLLA-based elements to which each pair of marker is attached are regions of low strain, and wherein the PLLA-based elements of the markers do not compromise the mechanical integrity of the stent.

2. A method of crimping a stent on a balloon, comprising:
    (a) providing a biodegradable polymeric stent, wherein the material from which structural elements of the stent are made consist of poly(D, L-lactide) or poly (D, L-lactic acid) (PDLLA);
    (b) attaching markers to the polymeric stem to provide capability of obtaining images of the polymeric stent with an imaging device during and after implantation of the stent in a vessel,
    wherein the stent consists of two pairs of markers, two of the markers being attached in an adjacent configuration about a proximal most end ring of the stent, and the remaining two markers being attached in an adjacent configuration about a distal most end ring of the stent, with the proviso that the stent has no other markers but for the four markers to allow for imaging of the polymeric stent and with a further proviso that an entire length of the stem between the first pair and second pair of markers is devoid of any markers, wherein a center point of a first marker is positioned at a circumferential distance from a center point of its adjacent second marker, wherein a center point of a third marker is positioned at a circumferential distance from a center point of its adjacent fourth marker, and wherein the pair of markers about the proximal most end ring of the polymeric stent are circumferentially off-set from the pair of markers about the distal most end ring of the polymeric stent; and (c) crimping the stent on a balloon of a catheter assembly by application of a crimping pressure to the stent positioned over the balloon, wherein when the crimping pressure is applied to the stent, the stent has regions of low strain and regions of high strain, such that PDLLA elements to which each pair of marker is attached are regions of low strain, and wherein the PDLLA elements of the markers do not compromise the mechanical integrity of the stent.

3. A method of crimping a stent on a balloon, comprising:
(a) providing a biodegradable polymeric stent, wherein the material from which structural elements of the stent are made consists of a lactide or lactic acid polymer ("lactide-based polymer");
(b) attaching markers to the lactide-based polymeric stent to provide capability of obtaining images of the lactide-based polymeric stent with an imaging device during and after implantation of the stent in a vessel, wherein the stent consists of two pairs of markers, two of the markers being attached in an adjacent configuration about a proximal most end ring of the stent, and the remaining two markers being attached in an adjacent configuration about a distal most end ring of the stent, with the proviso that the stent has no other markers but for the four markers to allow for imaging of the lactide-based polymeric stent and with a further proviso that an entire length of the stent between the first pair and second pair of markers is devoid of any markers, wherein a center point of a first marker is positioned at a circumferential distance from a center point of its adjacent second marker, wherein a center point of a third marker is positioned at a circumferential distance from a center point of its adjacent fourth marker, and wherein the pair of markers about the proximal most end ring of the polymeric stent are circumferentially off-set from the pair of markers about the distal most end ring of the polymeric stent; and (c) crimping the stent on a balloon of a catheter assembly by application of a crimping pressure to the stent positioned over the balloon, wherein when the crimping pressure is applied to the stent, the stent has regions of low strain and regions of high strain, such that lactide-based elements to which each pair of marker is attached are regions of low strain, and wherein the lactide-based elements of the markers do not compromise the mechanical integrity of the stent.

\* \* \* \* \*